(12) United States Patent
Endo et al.

(10) Patent No.: US 8,128,771 B2
(45) Date of Patent: Mar. 6, 2012

(54) METHOD OF PRODUCING CLOTHING ARTICLE

(75) Inventors: Masanori Endo, Tochigi (JP); Kenji Ando, Tochigi (JP); Shinnosuke Morita, Tochigi (JP); Takuo Yanashima, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/593,256

(22) PCT Filed: Mar. 26, 2008

(86) PCT No.: PCT/JP2008/055748
§ 371 (c)(1),
(2), (4) Date: Nov. 16, 2009

(87) PCT Pub. No.: WO2008/123310
PCT Pub. Date: Oct. 16, 2008

(65) Prior Publication Data
US 2010/0059168 A1     Mar. 11, 2010

(30) Foreign Application Priority Data

Mar. 28, 2007   (JP) .................................. 2007-86027

(51) Int. Cl.
*B29C 65/00*   (2006.01)
*B32B 37/00*   (2006.01)

(52) U.S. Cl. ........ 156/164; 156/160; 156/163; 156/183; 156/229; 156/324; 156/494; 156/495; 156/496

(58) Field of Classification Search .................. 156/160, 156/163, 164, 183, 229, 324, 494–496
See application file for complete search history.

(56) References Cited

U.S. PATENT DOCUMENTS

| 5,560,793 | A | 10/1996 | Ruscher et al. |
| 6,784,125 | B1 | 8/2004 | Yamakawa et al. |
| 6,994,763 | B2 * | 2/2006 | Austin .......................... 156/181 |
| 2004/0040642 | A1 * | 3/2004 | Otsubo et al. ................. 156/163 |
| 2005/0056678 | A1 | 3/2005 | Nomura et al. |

(Continued)

FOREIGN PATENT DOCUMENTS

JP        6-296638 A    10/1994

(Continued)

OTHER PUBLICATIONS

English translation of International Preliminary Report on Patentability (Form PCT/IB/338 and 373) and Written Opinion of the International Searching Authority issued on Oct. 29, 2009 in PCT/JP2008/055748.

*Primary Examiner* — Katarzyna Wyrozebski Lee
*Assistant Examiner* — Carson Gross
(74) *Attorney, Agent, or Firm* — Birch, Stewart, Kolasch & Birch, LLP

(57) ABSTRACT

A method of producing a clothing article including the steps of (a) joining first continuous webs 120*a* and 120*b* having stretchability in the longitudinal direction thereof both in a longitudinally stretched state along an edge portion thereof to a longitudinally substantially inextensible second continuous web 120*c* to make a continuous composite sheet 120, (b) joining the composite sheet 120 obtained in step (a) on its side to a member 130 of the clothing article to make a web assembly 110, and (c) cutting the web assembly 110 obtained in step (b) to length.

10 Claims, 7 Drawing Sheets

U.S. PATENT DOCUMENTS

| | | | |
|---|---|---|---|
| 2005/0126689 A1* | 6/2005 | Thorson et al. | 156/164 |
| 2009/0035527 A1 | 2/2009 | Kobayashi et al. | |
| 2009/0211070 A1* | 8/2009 | Schneider | 26/98 |

FOREIGN PATENT DOCUMENTS

| | | |
|---|---|---|
| JP | 7-285714 A | 10/1995 |
| JP | 11-276523 A | 10/1999 |
| JP | 2001-129016 A | 5/2001 |
| JP | 2001-254257 A | 9/2001 |
| JP | 2002-46204 A | 2/2002 |
| JP | 2002-172136 A | 6/2002 |
| JP | 2003-339768 A | 12/2003 |
| JP | 2004-262556 A | 9/2004 |
| JP | 2005-279077 A | 10/2005 |
| WO | WO-03/070140 | 8/2003 |
| WO | WO-2005/060900 A1 | 7/2005 |
| WO | WO 2006/036090 A1 | 4/2006 |

* cited by examiner

METHOD OF PRODUCING CLOTHING ARTICLE

TECHNICAL FIELD

The present invention relates to a method of producing a clothing article.

BACKGROUND ART

Disposable pull-on diapers having not only elasticized waist and leg opening edge portions but an elasticized below-waist portion (a portion below the waist opening edge portion) are known.

An elasticized below-waist portion of a disposable diaper is usually obtained by securing an elastic member in thread or tape form in its stretched state between two substantially inextensible sheets with an adhesive and allowing the elastic member to retract to gather the sheets. For example, Patent Document 1 discloses a method of producing a pull-on diaper including the steps of securing an elastic member for elasticizing a below-waist portion in its stretched state between two moving webs to make an outer cover elasticized in the machine direction in continuous form, spacedly fixing absorbent bodies to the outer cover of continuous form, and cutting the web assembly into individual diapers.

A stretch sheet that can be obtained without gathering a sheet material is known for use as a clothing material. In the cases where disposable diapers are produced using in a transverse feed system (a system in which a continuous web assembly having diapers continuous in the diaper transverse direction is cut into individual diapers) using such a stretch sheet, especially a highly extensible continuous stretch sheet, with its stretchable direction coincide with the machine direction, the stretch sheet is extended by the tension applied thereto while moving, and the extension percentage varies with variation of the tension. This being the case, it is difficult to stably produce disposable pull-on diapers with good finish accuracy because of positioning error or misalignment in, for example, bonding an absorbent body to the stretch sheet, making a leg hole through the stretch sheet, folding the stretch sheet in two, and joining the folded panels of the stretch sheet along predetermined seal lines.

It is conceivable to feed the stretch sheet without substantially causing the sheet to stretch in the longitudinal direction as proposed in Patent Document 2, but this requires impractically large equipment.

Patent Document 1: JP 6-296638
Patent Document 2: WO03/070140A1

DISCLOSURE OF THE INVENTION

The present invention provides a method of producing a clothing article. The method includes the steps of (a) joining a first continuous web having stretchability in its longitudinal direction in a longitudinally stretched state along an edge portion thereof to a longitudinally substantially inextensible second continuous web to make a continuous composite sheet, (b) joining the composite sheet obtained in step (a) on one side thereof to a member of the clothing article to make a web assembly, and (c) cutting the web assembly obtained in step (b) to length.

DETAILED DESCRIPTION OF THE INVENTION

The present invention will be described based on its preferred embodiments with reference to the accompanying drawing.

Figure 1:
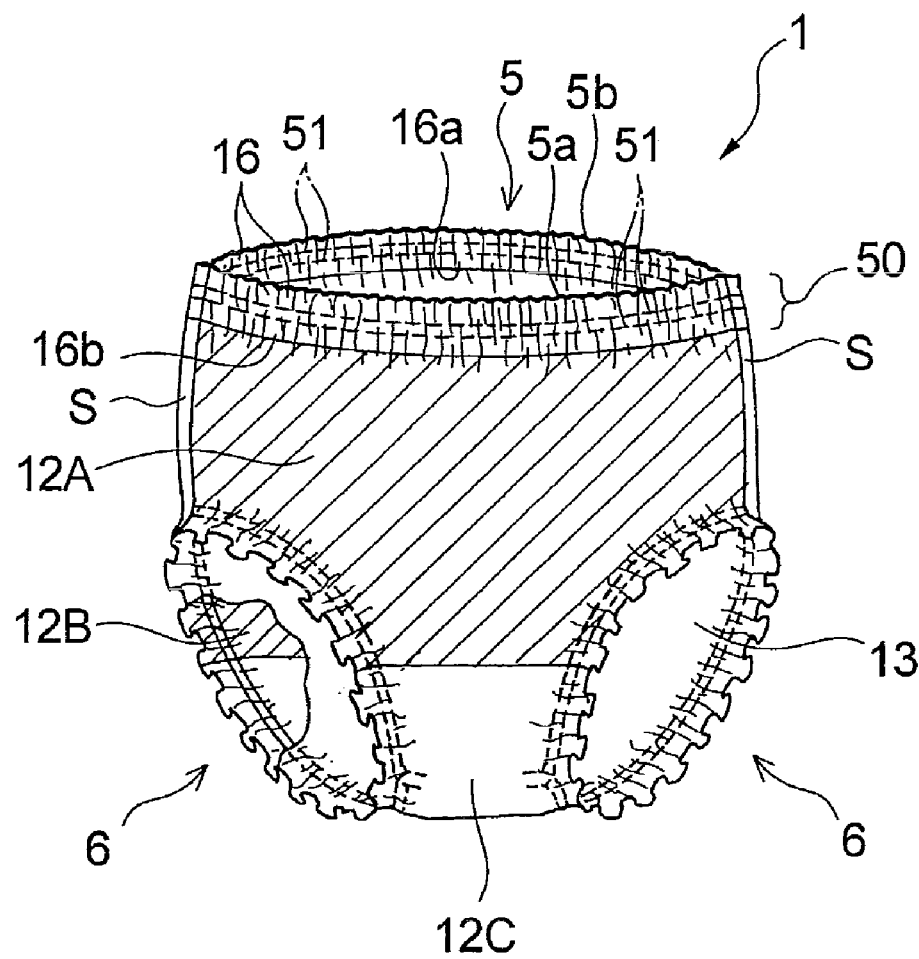
FIG. 1 is a perspective of a disposable pull-on diaper, an example of a clothing article produced by the method of the invention, with part cut away.

A clothing article produced by an embodiment of the invention will be described. In the present embodiment, a disposable pull-on diaper 1 (hereinafter also abbreviated as a diaper 1) illustrated in FIGS. 1 through 3 is produced.

Figure 2:
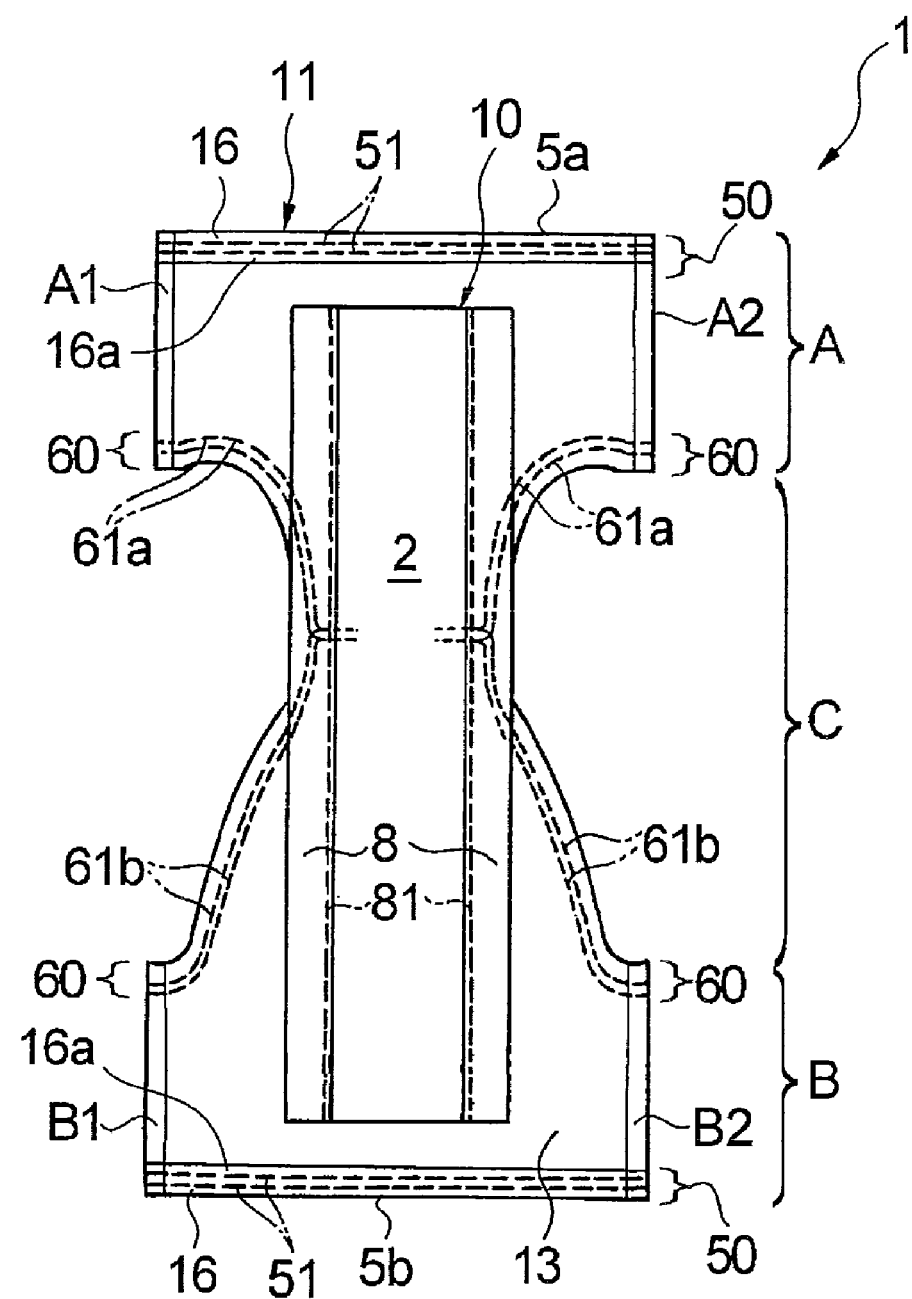
FIG. 2 is a plan of the disposable diaper of FIG. 1 in its flat-out state.
Figure 3:
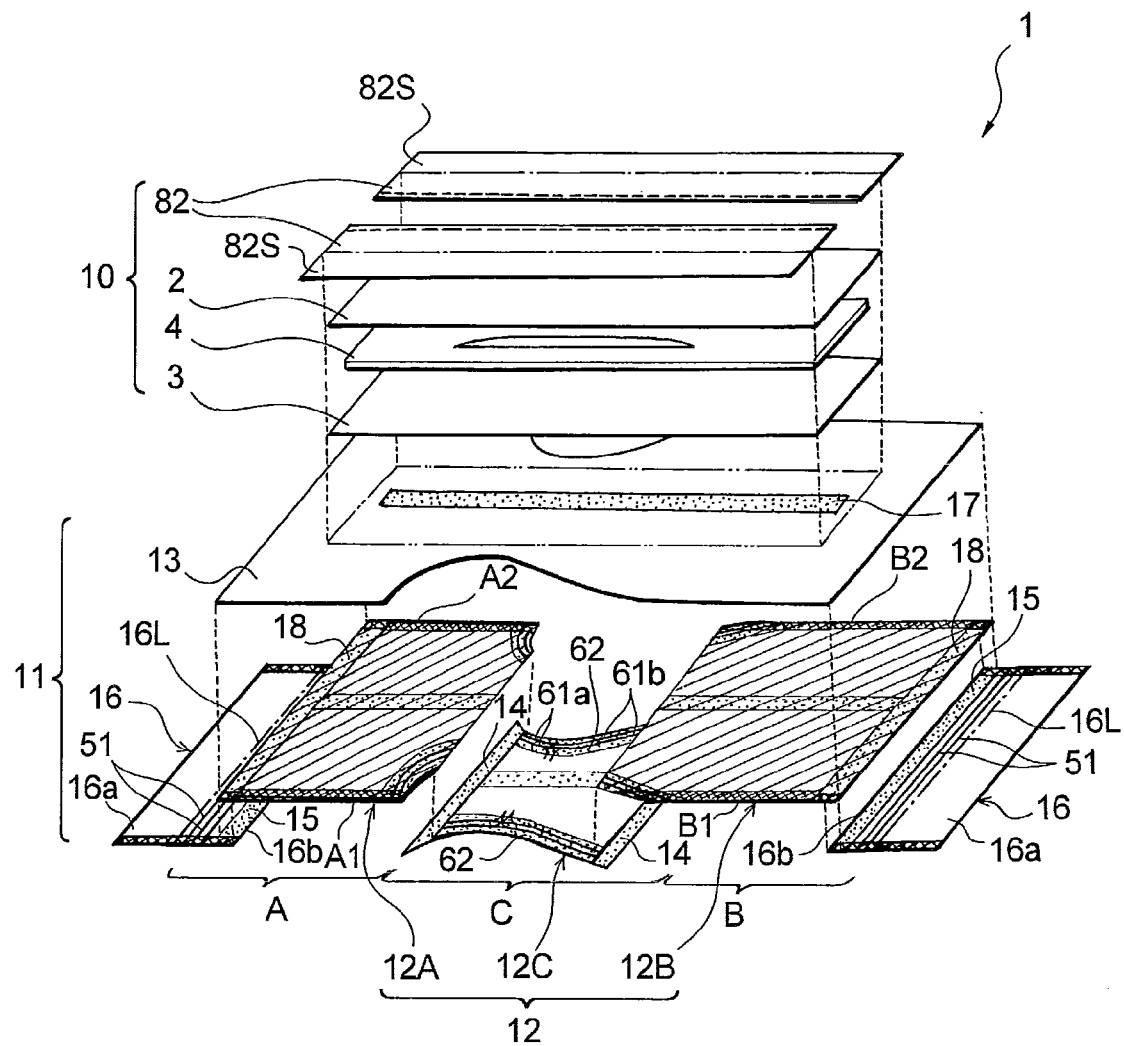
FIG. 3 is an exploded perspective of the disposable diaper shown in FIG. 1.

As illustrated in FIGS. 2 and 3, the diaper 1 includes an absorbent body 10 that is substantially oblong. The absorbent body 10 includes a liquid permeable topsheet 2, a liquid impermeable or hardly liquid permeable (or water repellent) backsheet 3, and a liquid retentive absorbent core 4 interposed between the sheets 2 and 3. The diaper 1 also includes an outer cover 11 disposed on the side of the backsheet 3 (i.e., the garment facing side) of the absorbent body 10.

As illustrated in FIG. 2, the diaper 1 is divided into a front portion A located on the stomach side of a wearer, a rear portion B located on the back side of a wearer, and a crotch portion C located therebetween. The outer cover 11 defines the contour of the diaper 1 and, in its flat-out uncontracted state, has a longitudinally middle portion thereof narrowed to have the shape of a sandglass. In the outer cover 11 both side edges A1 and A2 of the outer cover 11 in the front portion A and both side edges B1 and B2 of the outer cover in the rear portion B are joined to each other to make a pair of side seals S, S, thereby to form a waist opening 5 and a pair of leg openings 6, 6 of the diaper 1.

The absorbent body 10 is formed by uniting the topsheet 2, the backsheet 3, and the absorbent core 4. The topsheet 2, the backsheet 3, and the absorbent core 4 are of conventional types commonly used in the art. For example, the topsheet may be nonwoven fabric of various kinds or perforated film. The backsheet may be a resin film or a nonwoven fabric laminated with a resin film. The absorbent core 4 may be an aggregate made up of superabsorbent polymer particles and a fibrous material and wrapped in tissue (not shown).

A side cuff 8 formed of a liquid resistant or water repellent and air permeable material is provided along both sides edges of the absorbent body 10 as illustrated in FIG. 2. At least one elastic member 81 is disposed in its stretched state along near the free edge of each side cuff 8. While the disposable diaper 1 is worn by a wearer, the side cuffs 8 rise to impede the lateral flow of a body fluid. The side cuff 8 is formed of a cuff-forming sheet 82 as shown in FIG. 3. The cuff-forming sheet 82 extends laterally outward from the absorbent core 4 to provide an extension 82S, which, in an assembled state, wraps around beneath the absorbent core 4 and is secured between the absorbent core 4 and the backsheet 3 or between the backsheet 3 and an inner sheet 13 described below.

The outer cover 11 has a laminate structure composed of an outer sheet 12 and an inner sheet 13 which is disposed on the side of the absorbent body 10 of the outer sheet 12.

As illustrated in FIGS. 2 and 3, the outer sheet 12 is composed of a front outer subsheet 12A located in the front portion A, a rear outer subsheet 12B located in the rear portion B, and a crotch outer subsheet 12C located in the middle part of the crotch portion C. The crotch outer subsheet 12C is joined along its front end and rear end to the end of the front outer subsheet 12A and the end of the rear outer subsheet 12B, respectively, with an adhesive 14.

The inner sheet 13 is continuous from the front portion A through the crotch portion C to the rear portion B.

An edge portion (waist portion) 50 along the waist opening 5 in each of the front portion A and the rear portion B of the diaper 1 has a plurality of waist elastic members 51, 51 disposed along the opening edges (waist edges) 5a and 5b of the waist opening 5.

In the diaper 1, the waist elastic members 51, 51 are disposed as held or fixed by a waist edge-forming sheet 16 that is disposed in the edge portion (waist portion) 50 in each of the front portion A and the rear portion B of the diaper 1.

More specifically, as illustrated in FIG. 3, the waist edge-forming sheet 16 is a rectangle with its length extending in the diaper lateral direction over the whole width of the front portion A or the rear portion B. The waist edge-forming sheet 16 is folded in two along a folding line 16L. The folding line 16L corresponds to the opening edge (waist edge) 5a or 5b defining the waist opening 5. Between the facing panels of the thus folded waist edge-forming sheet 16 are secured the waist elastic members 51, 51 with an adhesive (not shown).

The skin facing panel 16a of the waist edge-forming sheet 16 located the inside of the diaper 1 is bonded to the skin facing side (the side adapted to face the skin of a wearer while worn) of the inner sheet 13 with an adhesive (not shown), while the garment facing panel 16b located the outside of the diaper 1 is bonded to the garment facing side (the side adapted to face the opposite to the skin of a wearer while worn) of the front outer subsheet 12A or the rear outer subsheet 12B, specifically the front end portion of the front outer subsheet 12A along the waist edge 5a or the rear end portion of the rear outer subsheet 12B along the waist edge 5b, with an adhesive 15.

The outer sheet 12 and the inner sheet 13 of the diaper 1 are bonded to each other along the side edges A1, A2, B1, and B2 by heat sealing, high frequency sealing or ultrasonic sealing. They are also bonded to each other along edges 60 of the leg openings 6 with an adhesive 62. The edge portions on the skin facing side of the front outer subsheet 12A and the rear outer subsheet 12B located near the edges 5a, 5b and the inner sheet 13 are also bonded via an adhesive 18. The outer sheet 12 and the inner sheet 13 are not bonded together for the most part of the area other than the parts described above. More specifically, the outer sheet 12 and the inner sheet 13 are bonded together in the parts described above and, in addition, in the laterally middle part extending in the diaper longitudinal direction. The outer sheet 12 and the inner sheet 13 are not joined in other than these parts.

The outer sheet 12 and the inner sheet 13 being not joined over a large area in the front portion A and the rear portion B of the diaper 1 offer the following advantages. Hindrance to stretch of the outer sheet 12 by an applied adhesive is minimized so that the rear portion B and the front portion A exhibit good stretch to provide a snug fit against a wearer's body while worn. The area in which the outer cover 11 becomes stiff due to an adhesive applied being so minimized, the diaper feels soft and pleasant to the touch on both the exterior surface thereof and the exposed interior surface of the outer cover 11 which is the part uncovered by the absorbent body 10. When the outer sheet 12 and the inner sheet 13 are formed of breathable material, such as nonwoven fabric, there is provided a diaper having good breathability and thereby capable of controlling the inside humidity. The same advantages may also be obtained by applying an adhesive not solid but in dots or by applying a fibrous adhesive as a porous coating almost all over the facing area of the two sheets. In such cases, the outer sheet and the inner sheet, being bonded together almost all over, provide increased laminate sheet strength.

A peripheral portion 60 along each of the leg openings straddling the front portion A, the crotch portion C and the rear portion B has leg elastic members 61a and 61b disposed along the edge of the leg opening. The leg elastic members 61a and 61b are secured between the outer sheet 12 and the inner sheet 13 in their stretched state by the adhesive 62.

A preferred method for continuously producing the disposable pull-on diaper 1 as an embodiment of the invention will be described by way of FIG. 4.

In the present method, a first continuous web 120a and a first continuous web 120b both stretchable in the longitudinal direction (i.e., the machine direction (MD)) are used to provide the front outer subsheet 12A and the rear outer subsheet 12B, respectively; a second continuous web 120c, a second continuous web 160a, and a second continuous web 160b each of which is substantially inextensible in the longitudinal direction (i.e., MD) are used to provide the crotch outer subsheet 12C and the opposing waist edge-forming sheets 16, 16, respectively; and a third continuous web 130 substantially inextensible in the longitudinal direction (i.e., MD) is used to provide the inner sheet 13.

The first continuous webs 120a and 120b may be longitudinally stretchable sheet webs prepared separately from the line of diaper manufacturing. In the present embodiment, however, the step of stretching the first continuous webs 120a and 120b is preceded by the step of processing non-stretch webs 120' to develop stretchability or the step of processing low-stretch webs 120' to enhance the stretchability to obtain the first continuous webs 120a and 120b as illustrated in FIG. 4. The thus obtained first continuous webs 120a and 120b are stretched.

Figure 4:
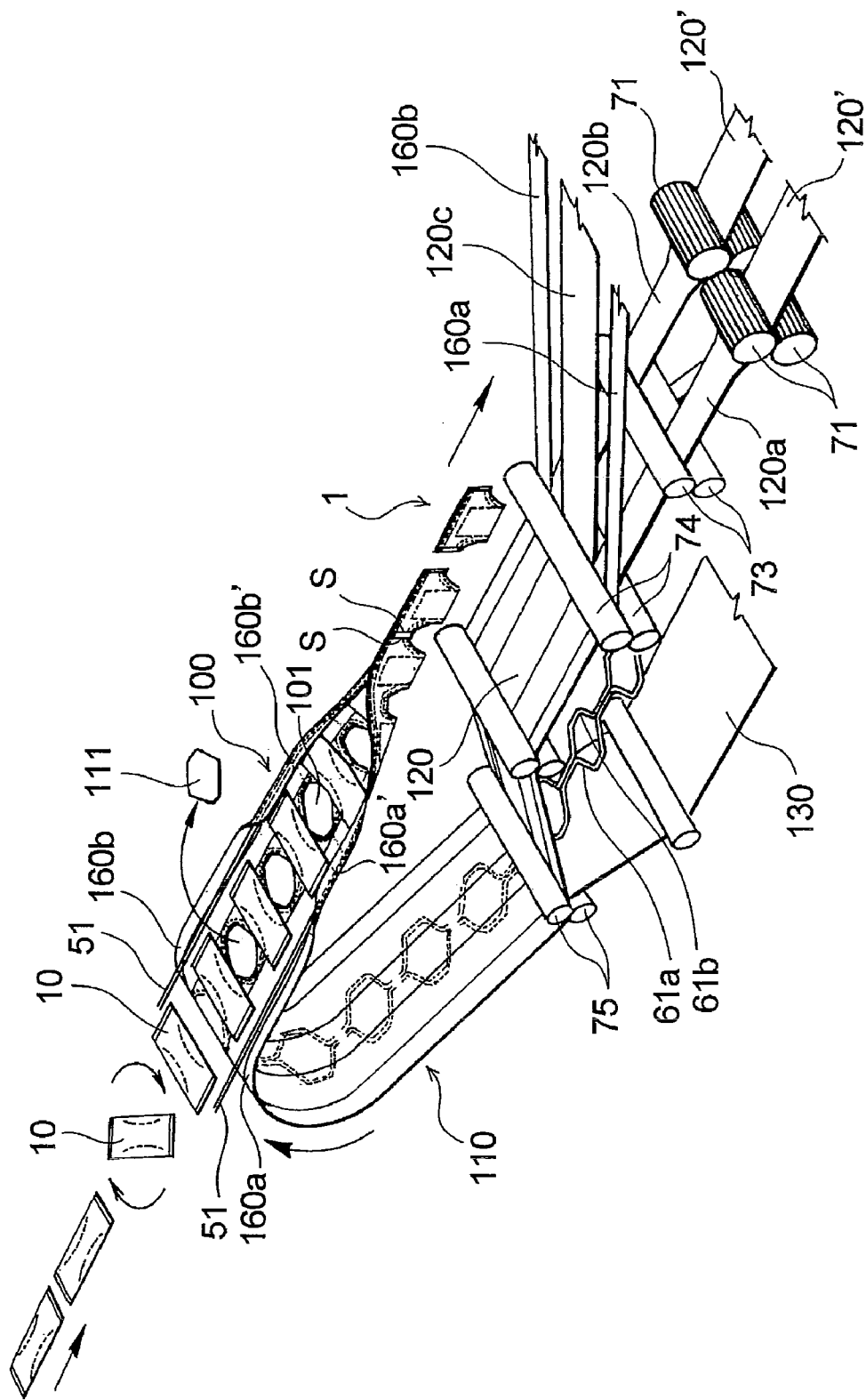
FIG. 4 is a schematic illustration of an embodiment of the invention, in which the disposable diaper of FIG. 1 is produced.

As illustrated in FIG. 4, the processing for stretchability development or enhancement used in the present embodiment is in-line processing using a pair of intermeshing corrugated rolls 71. More specifically, the processing is carried out by introducing a continuous web 120' composed of an elastic layer (e.g., an elastic fiber layer, an elastic net sheet or an elastic film) and an inelastic fiber layer on one or both sides of the elastic layer into the nip between the corrugated rollers 71, whereby the inelastic fiber layer is cut, the constituent fibers of the inelastic fiber layer are extended, or the interfiber fusion bonds in the inelastic fiber layer are destroyed. As a result, the inelastic fiber layer is converted into a structure that hardly impedes the stretch of the elastic layer. By this conversion, there is obtained the first continuous webs 120a and 120b with developed or enhanced stretchability. Each of the corrugated rollers 71 has a number of ridges (teeth) extending in the axial direction spacedly arranged on its periphery, providing grooves between adjacent ridges.

The thus provided first continuous webs 120a and 120b are continuously fed and stretched in the longitudinal direction between the pair of corrugated rollers 71 and a pair of nip rollers 73. The first continuous webs 120a and 120b in their stretched state are joined to the second continuous webs 120c, 160a, and 160b by overlapping the edge portions of adjoining webs and bonding them with an adhesive.

More specifically, one edge portion of the second continuous web 160a as a precursor of a waist edge-forming sheet 16 of the front section A is overlapped on one edge portion of the first continuous web 120a as a precursor of the front outer subsheet 12A, and one edge portion of the second continuous web 120c as a precursor of the crotch outer subsheet 12C is overlapped on the other edge portion of the first continuous web 120a. Likewise, one edge portion of the second continuous web 160b as a precursor of a waist edge-forming sheet 16 of the rear section B is overlapped on one edge portion of the first continuous web 120b as a precursor of the rear outer subsheet 12B, and the other edge portion of the second continuous web 120c as a precursor of the crotch outer subsheet 12C is overlapped on the other edge portion of the first continuous web 120b. The adjoining webs do not overlap other than their edge portions.

The adjoining webs are joined to each other in their overlapping edge portions.

In the present embodiment, in order to join the adjoining webs each other in their overlapping edge portions, an adhesive is applied to at least one of the facing sides of the edge portions before the overlapping, and the overlapped edge portions are pressed between a pair of pressure rollers 74. By joining the edge portions with an adhesive, the joined portions are soft, and a clothing article with good hand is obtained.

The adhesive is preferably applied such that the edge portions of adjoining webs are continuously bonded together in their longitudinal direction. Any adhesive applicator conventionally used in the production of this type of articles may be used with no restriction to apply the adhesive.

The extension percentage of the first continuous webs 120a and 120b being joined to the second continuous webs 120c, 160a, and 160b may be, for example 10% to 200%, preferably 20% to 150%, more preferably 30% to 120%. The extension percentage is defined to be [(length after extension−length before extension)/(length before extension)]×100. When an original length of 50 mm is extended to 100 mm or 150 mm, the extension percentage is 100% or 200, respectively.

The width of the edge portions of the first continuous web and the second continuous web to be joined together is desirably as small as possible. Taking into consideration strength of the resulting patched sheet and stability of processing, nevertheless, the width is preferably 5 to 50 mm, more preferably 5 to 20 mm.

As a result of the joining, there is obtained a broader composite sheet in which the second continuous web 160a, the first continuous web 120a, the second continuous web 120c, the first continuous web 120b, and the second continuous web 160b are adjoined in this order in the direction perpendicular to the MD (i.e., cross-machine direction).

The composite sheet 120 is superposed on a separately fed third continuous web 130 as a precursor of the inner sheet 13 and joined together via an adhesive. As illustrated in FIG. 4, the composite sheet 120 and the third web 130 are joined with leg elastic members 61a and 61b held therebetween. Specifically, an adhesive for securing the elastic members is applied to one or both of the facing sides of the webs 120 and 130 before the superposing, the elastic members 61a and 61b are introduced therebetween in their stretched state, and the two webs having the elastic members therebetween are pressed between the nip rollers 75. Alternatively, the adhesive for securing the elastic members may be applied to the elastic members 61a and 61b or both the elastic members 61a and 61b and the composite sheet 120 and/or the third web 130. To apply the adhesive for joining the two webs 120 and 130, any applicator conventionally used in the production of this type of articles may be used with no particular restriction.

Joining the composite sheet 120 and the third continuous web 130 provides a continuous-form outer cover 110 (composite laminate). A continuous-form absorbent body is cut into individual absorbent bodies 10, which are turned 90° and spacedly fixed on the continuous-form outer cover 110. The unnecessary part 111 corresponding to a leg opening is cut out of the continuous-form outer cover 110 with, for example, a rotary cutter or a laser cutter to make a continuous-form diaper 100.

An adhesive is applied to both edge portions formed of the second continuous webs 160a and 160b of the continuous-form outer cover 110 or the continuous-form diaper 100. Waist elastic members 51 are disposed on the edge portions where the adhesive is applied, and the edge portions 160a' and 160b' of the second continuous webs 160a and 160b, respectively, are folded over the third continuous web 130 and secured thereto.

The continuous-form diaper 100 is then folded in two. The folded continuous-form diaper 100 is sealed to form side seals S, S by heat sealing, ultrasonic sealing, high frequency sealing or like means, and the continuous-form diaper 100 is cut into individual disposable pull-on diapers 1 after or simultaneously with the formation of the side seals S, S.

Otherwise, the diaper 1 can be produced in a usual manner for the production of disposable pull-on diapers in a transverse feed system. The adhesive 17 for fixing the absorbent body 10 to the continuous-form outer cover 110 may be applied to either one or both of the absorbent body 10 and the continuous-form outer cover 110. Removal of the unnecessary part 111 for making the leg opening may be carried out before fixing the absorbent body 10 to the continuous-form outer cover 110.

According to the present embodiment, the diaper 1 having the above described structure can be produced efficiently in a continuous manner.

According to the method of the present embodiment, a disposable pull-on diaper exhibiting good stretchability in its below-waist portion in the front portion A and the rear portion B can be produced with high finish accuracy in a stable continuous manner despite of using the first continuous webs 120a and 120b having stretchability in the longitudinal direction.

If the first continuous webs 120a and 120b as precursors of the rear outer subsheet and the front outer subsheet, respectively, are fed by themselves, they easily vary in extension percentage with variation of tension applied thereto while moving because of their longitudinal stretchability. Then, when they are processed, e.g., cut, folded, or combined with other members, positioning error or reduction in processing accuracy is likely to occur with variation in tension in cutting, folding, bonding, or other processing operations.

According to the method of the present embodiment, in contrast, since the first continuous webs 120a and 120b are joined in their stretched state along their edge portions to substantially inextensible second webs 120c, 160a, and 160b into a composite sheet 120, the resulting composite sheet 120 hardly extends any further or, may extend slightly but suddenly stop extending further only if it is moved under such a tension that prevents the retractability of the first continuous webs 120a and 120b from contracting the composite sheet 120. Therefore, as long as the composite sheet 120 is placed under at least a certain tension in the moving direction, its extension percentage hardly varies even if the tension applied thereto fluctuates during the movement. As a result, the positioning accuracy or finishing accuracy are improved in various processing operations, such as cutting, folding and joining with other members. According to the present embodiment, in particular, since each of the first continuous webs 120a and 120b is adjoined along both edge portions thereof to substantially inextensible webs, the composite sheet 120 undergoes little variation in extension percentage with variation in tension while moving.

As described, the method of the present embodiment allows for various processing operations with good accuracy thereby to produce a disposable pull-on diaper (a kind of clothing articles) having good stretchability precisely, stably, and continuously. When compared with using an integral outer sheet 12 formed of a stretch sheet material, the composite outer sheet 12 requires a reduced amount of a stretch sheet material. This leads to reduction of material cost because a stretch sheet material is generally more expensive than a substantially inextensible sheet material. Moving a stretch sheet as joined with a substantially inextensible sheet which is a member of the clothing article not only reduces the required amount of the extensive stretch sheet but avoids the necessity of a moving mechanism specialized to control the variation of the stretch sheet, thereby enabling the production without requiring excessively large equipment.

In the above described embodiment, after the composite sheet 120 is joined to the substantially inextensible third continuous web as a precursor of the inner sheet 13 to form the continuous-form outer cover 110, the continuous-form outer cover 110 or a continuous-form diaper 100 is subjected to further processing. As stated, since the composite sheet 120 undergoes little variation in extension percentage with variation in tension, the processing of the continuous-form outer cover 110 and the continuous-form diaper 100 can be performed with the same high accuracy as described.

That is, misalignment or positioning error is prevented in, for example, placing the absorbent body 10 on the continuous-form outer cover 110, making a leg hole 101 through the continuous-form outer cover 110 before or after placement of the absorbent body 10, folding the continuous-form outer cover 110 having the absorbent body 10 fixed thereto (i.e., the continuous-form diaper 100), sealing the continuous-form outer cover 110 having the absorbent body 10 fixed thereto (i.e., the continuous-form diaper 100) at a predetermined positions to form a side seal S, and cutting the continuous-form diaper 100 into individual diapers. Disposable pull-on diapers with high finish accuracy can thus be produced stably in a continuous manner.

While in the present embodiment the third continuous web as a precursor of the inner sheet is substantially inextensible, the same effects as described are obtained even when a longitudinally extensible web is used as a precursor of the inner sheet because of little variation in extension percentage of the composite sheet 120 with variation in tension.

In the above described method of producing the disposable pull-on diaper 1, the first continuous webs 120a and 120b as precursors of the front outer subsheet 12A and the rear outer subsheet 12B, respectively, are webs having stretchability in the longitudinal direction (MD). On the other hand, the second continuous webs 160a and 160b as precursors of the waist edge-forming sheets 16 in the front portion A and the rear portion B, respectively, the second continuous web 120c as a precursor of the crotch outer subsheet 12C, and the third continuous web 130 as a precursor of the inner sheet 13 are webs having substantially no extensibility in the longitudinal direction (MD).

As used herein, the phrase "continuous web having stretchability in the longitudinal direction (also referred to as stretch sheet)" means a continuous sheet having ability to extent under tension in its longitudinal direction (MD) and retract on release from the tension. The stretch sheet preferably has a maximum elongation of at least 100% in the longitudinal direction and, when extended to an elongation of 100% in that direction, retract to a recovery (a recovery from 100% extension) of at least 70%.

The stretch sheet is preferably more extensible in its longitudinal direction (MD) than its transverse direction (the direction perpendicular to the longitudinal direction, i.e., CD). Specifically, it is preferred that the stretch sheet be extensible largely (having a maximum elongation of 100% or more) in the longitudinal direction and retractable (having a recovery from 100% extension of 70% or more) when released, while be extensible only slightly (e.g., having a maximum elongation of 50% or less) in the transverse direction.

As used herein, the phrase "continuous web having substantially no extensibility in the longitudinal direction (also referred to as non-stretch sheet)" means a continuous sheet having no or little extensibility even in a tensioned state during feed so that it undergoes little variation in extension percentage with variation in tension applied. The non-stretch sheet preferably has a maximum elongation of 10% or less in the longitudinal direction (MD) (the maximum length after stretch is only 1.1 times the original length), more preferably a maximum elongation of 8% or less in that direction. The non-stretch sheet preferably has a maximum elongation of 10% or less, more preferably 8% or less, in both the longitudinal direction and the direction perpendicular thereto.

Method of Measuring Recovery from Extension:

A 25 mm wide and 50 mm long specimen of a sheet is set on a tensilon tensile tester at an initial jaw separation of L0 and extended 100% to a length L2 (L2=L0×2) at a pulling rate of 300 mm/min. The specimen is then retracted at the same rate. When the tensile load returns to zero, the length L1 of the specimen (the length after recovery from extension) is measured. The recovery from 100% extension is calculated from the following formula:

$$\text{Recovery from 100\% extension}(\%) = [(L2-L1)/(L2-L0)] \times 100$$

Method of Measuring Maximum Elongation:

A specimen having the same dimension is elongated under the same condition as in the measurement of recovery from extension. The elongation at break is taken as a maximum elongation. The break point is defined as the point on the extension percentage vs. load curve at which the measured tensile load reaches its maximum value.

Various sheet materials with longitudinal stretchability may be used as the stretch sheet constituting the first continuous web. Preferred examples of the stretch sheet include (1) a sheet having an elastic fiber layer and an extensible fiber layer united to one or both sides of the elastic fiber layer, (2) a sheet having an elastic net sheet and an extensible fiber layer united to one or both sides of the elastic net sheet, (3) a sheet having an elastic film and an extensible fiber layer united to one or both sides of the elastic film, and (4) a stretch sheet having an extensible nonwoven fabric and a large number of elastic filaments arranged to extend in one direction without intersecting with each other and bonded to the extensible nonwoven fabric over their whole length in their substantially nonstretched state. Uniting the elastic fiber layer and the extensible fiber layer is carried out by, for example, entangling the fibers of the two fiber layers superposed on each other by hydroentanglement or through-air bonding or bonding the two fiber layers by heat embossing, applying an adhesive, or ultrasonication.

The sheet (1) is exemplified by (a) a stretch nonwoven fabric having an elastic fiber layer and an inelastic fiber layer, that is substantially inelastic, on at least one side of the elastic fiber layer. The elastic fiber layer and the inelastic fiber layer are joined together all over by fusion bonding at fiber intersections while the fibers constituting the elastic fiber layer remain in a fibrous form. The inelastic fiber layer has part of its fibers enter the elastic fiber layer and/or the elastic fiber layer has part of its fibers enter the inelastic fiber layer. Exemplary and preferred of the sheets (1), (2), and (3) include (b) a stretch sheet having an elastically stretchable elastic layer and an inelastic fiber layers that is substantially inelastic, the stretch sheet being obtained by superposing the two layers on each other, partially joining them, and stretching the resulting laminate sheet.

The stretch nonwoven fabric (a) is described in more detail. The fibers constituting the elastic fiber layer and the fibers constituting the inelastic fiber layer are fusion bonded to each other at their intersections on and near the interfaces between the elastic fiber layer and the inelastic fiber layer. Thus, the fiber layers are evenly joined together substantially all over their interfaces. Being joined all over, the fiber layers are prevented from separating from each other and forming a gap therebetween. Thus, the stretch nonwoven fabric has a multilayer structure and yet exhibits integrity like monolithic nonwoven fabric. By the expression "the constituent fibers of the elastic fiber layer remain in a fibrous form" is meant that most of the fibers constituting the elastic fiber layer are not in a cohesive film-like state or a cohesive film-like/fibrous mixed state even after application of heat, pressure and so forth. The elastic fiber layer has its fibers fusion bonded at their intersections throughout its thickness. Likewise, the inelastic fiber layer has its fibers fusion bonded at their intersections throughout their thickness.

In the case where the inelastic fiber layer is provided on both sides of the elastic fiber layer, at least one of the inelastic fiber layers has part of its constituent fibers enter the elastic fiber layer and/or the elastic fiber layer has part of its constituent fibers enter at least one of the inelastic fiber layers. In order to have the fibers of the inelastic fiber layer enter the elastic fiber layer and/or to have the fibers of the elastic fiber layer enter the inelastic fiber layer, it is desirable that at least one of the inelastic fibers and the elastic fibers be in the form of a web (i.e., a loose aggregate of fibers having no fusion bonds) before the step of fusion bonding the fibers of the inelastic fiber layer and the fibers of the elastic fiber layer. To help fibers of a layer to enter another layer, it is desirable that the web be made up of staple fibers for higher freedom of movement than continuous fibers.

A through-air process is preferred for having the fibers of the inelastic fiber layer enter the elastic fiber layer and/or having the fibers of the elastic fiber layer enter the inelastic fiber layer. A through-air process easily achieves having fibers of a layer enter another layer facing thereto and/or having a layer receive fibers from another layer facing thereto. A through-air process easily achieves having the fibers of the inelastic fiber layer enter the elastic fiber layer while retaining the bulk of the inelastic fiber layer. Especially in the cases where the fibers of the inelastic fiber layer are entangled with the fibers of the elastic fiber layer, it is preferred that the entanglement be achieved only by a through-air process. Fiber entanglement by a through-air process is preferably accomplished by properly adjusting the air blowing pressure, air velocity, basis weight and thickness of the fiber layers, the running speeds of the fiber layers, and so on. The through-air treatment is preferably carried out under specific conditions. When the inelastic fiber web and an elastic fiber web are treated with hot air (particularly in a through-air system), part of the fibers of the inelastic fiber web enter the elastic fiber web and, at the same time, the fibers of the inelastic fiber web and/or the fiber of the inelastic fiber web and the fibers of the elastic fiber web are fusion bonded at their intersections. In this situation, care should be taken that the fibers of the elastic fiber web do not assume a cohesive film-like state or a cohesive film-like/fibrous mixed state as a result of the hot air treatment.

The elastic fiber layer has the ability to extend under tension and retract or contract when released from the tension. When the elastic fiber layer is 100% elongated in at least one direction parallel to its plane and then retracted, the residual strain is preferably 20% or less, more preferably 10% or less. It is desirable that the elastic fiber layer has the recited residual strain in at least one of the MD and CD, particularly preferably in both the MD and CD.

The elastic fiber layer is an aggregate of elastic fibers. Methods of forming elastic fibers include a melt-blowing method in which a molten resin is extruded through orifices and the extruded molten resin streams are drawn by hot air into fine fibers, a spun bonding method in which a half-molten resin is drawn by cool air or by mechanical drawing, and a blow spinning method, which is a combination of a melt blowing method and a spun bonding method and may be said to be a modified melt blowing method. The elastic fiber layer may have the form of a web or nonwoven fabric made of elastic fibers by, for example, blow spinning, spun bonding or melt blowing. The elastic fiber layer is particularly preferably a web obtained by blow spinning. The fibers that can be used to constitute the elastic fiber layer include those made from thermoplastic elastomers or rubber. Thermoplastic elastomers are melt-spinnable using an extruder in the same manner as ordinary thermoplastic resins, and the fibers thus obtained are easy to fusion bond. Therefore, fibers of thermoplastic elastomers are particularly suited for making the stretch nonwoven fabric that has air-through nonwoven as a basic structure. Examples of the thermoplastic elastomers include styrene elastomers such as SBS, SIS, SEBS, and SEPS, olefin elastomers, polyester elastomers, and polyurethane elastomers. These elastomers may be used either individually or in combination of two or more thereof.

The inelastic fiber layer is extensible but substantially inelastic. The term "extensible" as used herein is intended to include not only a fiber layer whose constituent fibers per se are extensible but also a fiber layer whose constituent fibers are not per se extensible but which shows extensibility as a result of debonding of constituent fibers that have been fusion bonded at their intersections, change of a three-dimensional structure formed of a plurality of constituent fibers fusion-bonded to one another, or breaks of the constituent fibers. The fibers that can be used to constitute the inelastic fiber layer include fibers of polyethylene (PE), polypropylene (PP), polyesters (PET and PBT), and polyamides. The fibers constituting the inelastic fiber layer may be staple fibers or continuous fibers and hydrophilic or water repellent. Sheath-core or side-by-side conjugate fibers, split fibers, modified cross-section fibers, crimped fibers, and heat shrunken fibers are also useful. These fibers may be used either individually or in combination of two or more thereof. The inelastic fiber layer may be a web or nonwoven fabric of continuous filaments or staple fibers.

The stretch sheet (b) will be described in more detail. The stretch sheet is obtained by providing a laminate sheet having an elastically stretchable elastic layer and an inelastic fiber layer, which is substantially inelastic and bonded to one or both sides of the elastic layer in parts in a regular pattern, and stretching the laminate sheet.

The laminate sheet used to make the stretch sheet is prepared, for example, as follows. A fiber web (first inelastic fiber layer) is continuously fed from a carding machine. Elastic fibers are fed on the fiber web to form an elastic layer. A fiber web (second inelastic fiber layer) fed from another carding machine is continuously fed on the elastic layer. The resulting stack of three layers is subjected to a hot air treatment in a through-air system drier. The hot air treated laminate sheet is heat embossed through an embossing unit including an embossing roller having embossing projections regularly arranged on its peripheral surface and an anvil roller facing to the embossing roller. In the process described above, the hot air treatment in the drier is for causing the elastic fibers and the inelastic fibers to be fusion bonded or to mutually enter the adjoining fiber layer. The hot air treatment may be omitted.

The elastic layer preferably contains elastic fibers made from an elastic material. Elastic materials include thermoplastic elastomers, rubber, and ethylene-propylene copolymers. Thermoplastic elastomers are preferred of them; for they are relatively easily formed into elastic fibers. Examples of the thermoplastic elastomers include polyurethane elastomers, styrene elastomers (e.g., SBS, SIS, SEBS, and SEPS), olefin elastomers (e.g., ethylene; propylene or butene copolymers), vinyl chloride elastomers, and polyester elastomers. These elastomers may be used either individually or in combination of two or more thereof. The proportion of the elastic fibers made from an elastic material in the elastic layer is preferably 50% to 100% by weight, more preferably 75% to 100% by weight. The elastic layer may be a film or a net instead of the fiber layer. The film or net can be made from the above recited elastic materials.

The inelastic fiber layer is extensible but substantially inelastic. The term "extensible" as used herein is intended to include not only a fiber layer whose constituent fibers per se are extensible but also a fiber layer whose constituent fibers are not per se extensible but which shows extensibility as a result of debonding of constituent fibers that have been fusion bonded at their intersections, change of a three-dimensional structure formed of a plurality of constituent fibers fusion-bonded to one another, or breaks of the constituent fibers. The fibers that can be used to constitute the inelastic fiber layer include fibers of polyethylene, polypropylene, polyesters (PET and PBT), nylon and biodegradable resin such as polylactate. The fibers constituting the inelastic fiber layer may be staple fibers or continuous fibers and hydrophilic or water repellent. Sheath-core or side-by-side conjugate fibers, split fibers, modified cross-section fibers, crimped fibers, and heat shrunken fibers are also useful. These fibers may be used either individually or in combination of two or more thereof.

The stretch sheet (4) supra will be described in detail. The elastic filaments may be those formed by drawing a filamentous elastic resin in a molten or softened state at a draw ratio 1.1 to 400 (more preferably 4 to 100). The elastic resin is exemplified by thermoplastic elastomers and rubber. Thermoplastic elastomers are preferred materials because they are melt-spinnable using an extruder in the same manner as ordinary thermoplastic resins, and the filaments thus obtained are easy to fusion bond to nonwoven fabric. Various thermoplastic elastomers such as described above as a material of elastic fibers can be used. The thermoplastic elastomers may be used either alone or in combination of two or more thereof. Conjugate fibers having these resins in a sheath/core or side-by-side configuration are also useful. A styrene elastomer, an olefin elastomer, or a combination thereof is particularly preferred in terms of spinnability into elastic filaments, stretch characteristics, and cost.

The elastic filaments are bonded to the nonwoven fabric in a substantially nonstretched state. Modes of bonding the elastic filaments and the nonwoven fabric include fusion bonding and bonding using an adhesive. In a preferred mode, the elastic filaments are fusion bonded to the nonwoven fabric. It is preferred that the elastic filaments be sandwiched in and bonded to two nonwoven fabric layers which may be the same or different. The nonwoven fabric to which the elastic filaments are bonded is extensible in the same direction as the extending direction of the elastic filaments. The term "extensible" as used herein is intended to include not only nonwoven fabric whose constituent fibers per se are extensible but also nonwoven fabric whose constituent fibers are not per se extensible but which shows extensibility as a result of debonding of constituent fibers that have been bonded at their intersections, change of a three-dimensional structure formed of a plurality of constituent fibers bonded to one another, or breaks of the constituent fibers. The elastic filaments preferably have a diameter of 10 to 200 μm, more preferably 20 to 130 μm. In saying that the elastic filament is bonded to nonwoven fabric over the whole length thereof, it is not necessarily implied that all the fibers (of the fibers constituting the nonwoven fabric) in contact with an elastic filament should be bonded to the elastic filament 13 but it is meant that the elastic filaments and the fibers of the nonwoven fabric are bonded to each other without intentionally leaving part of them unbonded. Bonding the elastic filament to the nonwoven fabric over its whole length achieves sufficiently ensured adhesion between the elastic filaments and the nonwoven fabric. Thus the elastic filaments are prevented from separating from the nonwoven fabric when the stretch sheet is stretched. If the elastic filaments separate from the nonwoven fabric, the nonwoven fabric may lift to cause the stretch sheet to wrinkle in a natural state (i.e., relaxed state).

Various known stretch sheets can be used, including the nonwoven fabric formed of mixed fibers containing thermoplastic polyurethane elastomer fibers described in JP 2004-244791A, the extensible composite nonwoven fabric described in JP 9-512313A, the sheet proposed as "a stretchable topsheet for hygienic articles" in JP 3-269145A, the elastic stretch composite sheet described in JP 2001-18315A, the stretch composite nonwoven fabric described in JP 2001-140158A, the composite elastic nonwoven fabric disclosed in JP 9-500936A, and the laminate sheet described in JP 10-29259A.

Exemplary and preferred of the inextensible sheet for use as the second continuous webs are nonwoven fabric, laminates of nonwoven fabric and resin film, and porous film. Exemplary and preferred of the third continuous web that is substantially inextensible in the longitudinal direction are nonwoven fabric, laminates of nonwoven fabric and resin film, and porous film.

It is preferred that the method of producing a clothing article of the invention further include the step of transversely spreading, i.e., stretching, the composite sheet to correct a wrinkle or transverse contraction of the composite sheet prior to the step of joining the composite sheet with a member of the clothing article. In this case, it is preferred that the step of joining the composite sheet with a member of the clothing article be carried out with the composite sheet being in the transversely spread state.

Figure 5:
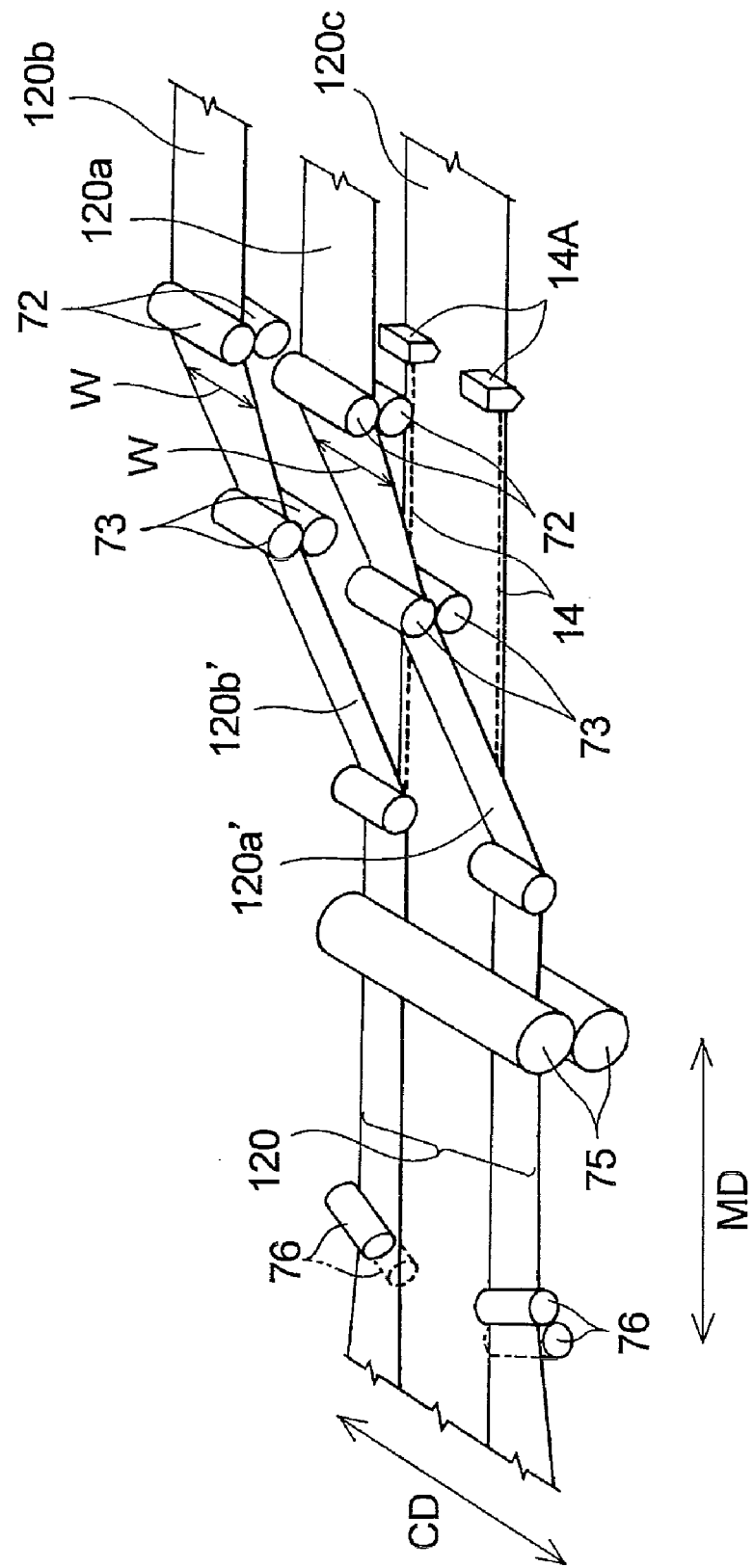
FIG. 5 illustrates an example of a preferred embodiment of the invention.

In an example shown in FIG. 5, a first continuous webs 120*a* and 120*b* having stretchability in the longitudinal direction are stretched between a first pair of nip rollers 72 and a second pair of nip rollers 73 and, as being in the stretched state, joined on their respective edge portions 120a' and 120b' to the respective edge portions of a second continuous web 120c that is substantially inextensible in the longitudinal direction. To achieve the joining, an adhesive 14 is applied by means of an applicator 14A, and the joined webs are pressed between a pair of nip rollers 75. There is obtained a composite sheet 120 as a precursor of the outer sheet 12 of an outer cover.

The first continuous webs 120a and 120b reduce in width W on being stretched. Since the composite sheet 120 has the first continuous webs 120a and 120b joined to the second continuous web 120c in their stretched state, it can wrinkle or reduce in width due to the retractability of the first continuous webs 120a and 120b when, for example, the longitudinal tension applied thereto is insufficient. If this is the case, the winkle or transverse contraction can easily be corrected by widening the composite sheet. The composite sheet with the wrinkle or transverse contraction thus corrected (in a state with the width restored to some extent or with the wrinkle almost eliminated) is fabricated together with other members of a clothing article, such as the web as a precursor of the inner sheet 13. Therefore, the correction step ensures the accuracy of the subsequent processing steps to provide a clothing article with improved finish accuracy.

In the example illustrated in FIG. 5, both the opposite edge portions of the composite sheet 120 pass between respective pairs of nip rollers 76 in an S-wrapped shape, whereby the composite sheet 120 is spread to correct any wrinkle or transverse contraction. Each pair of nip rollers 76, 76 are disposed with their axial direction inclined with respect to the direction perpendicular to the moving direction (MD) of the composite sheet 120 (i.e., the CD). The angle of inclination is preferably 0.1° to 20° to a line parallel to the CD (the angle of inclination of a line parallel to the CD is)0°.

The wrap angle (contact angle) of the web on one nip roller is preferably 3° to 180°, more preferably 3° to 135°, while depending on the outer diameter of the roller. Too large a wrap angle causes the web to serpentine, and too small a wrap angle results in insubstantial spreading of the web. The wrap angle is adjusted as appropriate to the material properties of the stretch sheet and a desired spread width.

While the invention has been described with particular reference to one embodiment, it should be understood that various changes and modifications can be made therein without departing from the spirit of the invention.

For example, in the above described embodiment, each of the first continuous webs 120a and 120b are joined along both edges thereof to the second continuous webs 120c and 160a or 160b, it may be joined along one of its edges to a second continuous web.

Figure 6:
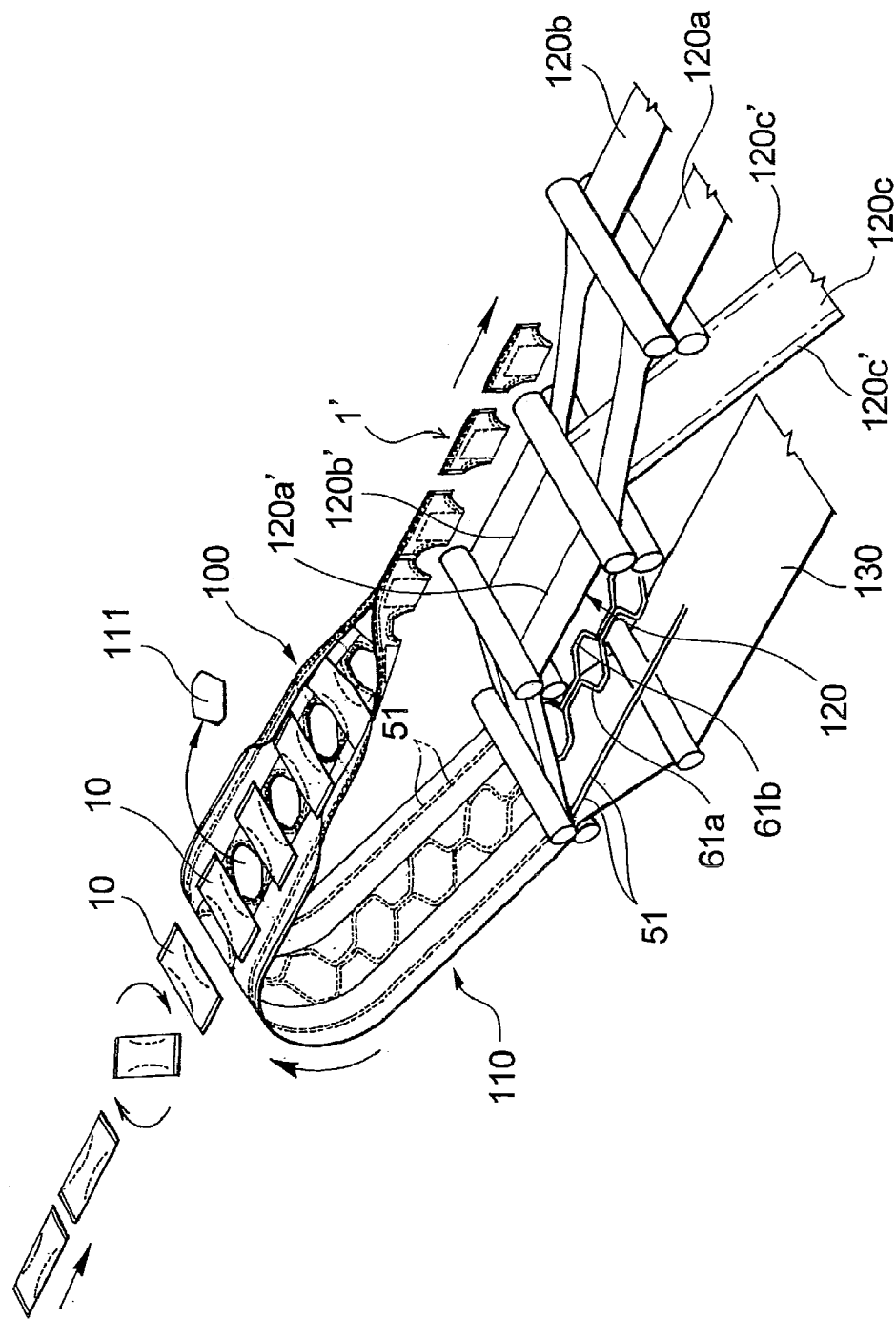
FIG. 6 illustrates another embodiment of the invention (equivalent to FIG. 4).

In FIG. 6 illustrating an embodiment of the method of producing a diaper 1', for instance, each of first continuous webs 120a and 120b is joined along one of its edge portion 120a' or 120b', respectively, to one of the edge portions 120c', 120c' of an inextensible second continuous web 120c as a precursor of the crotch outer subsheet 12C while leaving the other edge free, i.e., non-joined to an inextensible second continuous web like the second continuous webs 160a and 160b used in the first embodiment.

In the embodiment illustrated in FIG. 6, a composite sheet 120 composed of the second continuous web 120c and two first continuous webs 120a and 120b is used as a precursor of the outer sheet 12. The composite sheet 120 is joined with a substantially inextensible third continuous web 130 as a precursor the inner sheet 13. When the composite sheet 120 and the third continuous web 130 are joined, not only leg elastic members 61a and 61b but waist elastic members 51, 51 are held therebetween.

After an absorbent body 10 is secured to the continuous-form outer cover 110 obtained by joining the composite sheet 120 and the third continuous web 130, the opposite edge portions of the continuous-form outer cover 110, each of which is composed of the first continuous webs 120a and 120b and the third continuous web 130 extending from each longitudinal end of the absorbent body 10, are folded over the side of the absorbent body 10. The diaper 1' is produced otherwise in the same manner as in the above described method of producing the diaper 1.

Also included in the present invention is an embodiment in which one stretchable first continuous web and one substantially inextensible second continuous web are joined to form a continuous composite sheet.

Figure 7:
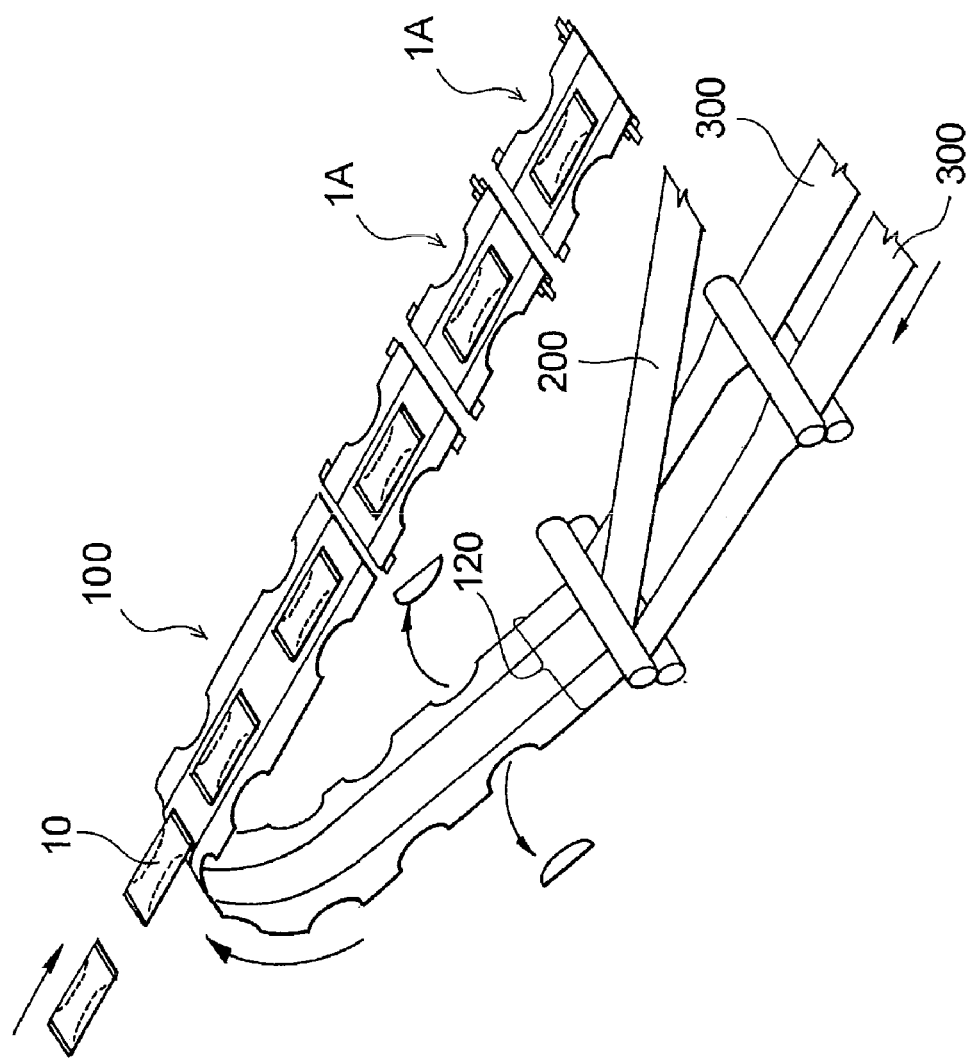
FIG. 7 illustrates still another embodiment of the invention (equivalent to FIG. 4).

While, in the above described embodiments, disposable diapers are produced in a transverse feed system (a system in which a continuous web assembly having diaper precursors continuous in the diaper transverse direction is formed), diapers may be produced in a longitudinal feed system (a system in which a continuous web assembly having diaper precursors continuous in the diaper longitudinal direction is formed) as illustrated in FIG. 7. As in the embodiment of FIG. 7, a composite sheet 120 composed of first continuous webs 300 and a second continuous web 200 may be used without being joined with other sheet web (third continuous web). In the embodiment of FIG. 7, the absorbent body 10 is "a member of a clothing article".

The object (the member of a clothing article) to which the composite sheet composed of the first and second continuous webs is joined on one side thereof is preferably another continuous sheet material. In the cutting step, the composite sheet and the other continuous sheet material joined thereto are preferably cut simultaneously.

In the embodiment illustrated in FIG. 7, stretchable first continuous webs 300, 300 are joined in their extended state to each of the opposing edge portions of a substantially inextensible second continuous web 200, respectively, via an adhesive (not shown, preferably a hot melt adhesive) to make a composite sheet 120. Both edge portions of the resulting composite sheet 120 are cut in an arc shape to form leg openings, and absorbent bodies 10 are secured on the composite sheet 120 at an interval. After attaching diaper fastening means, such as fastening tapes, the continuous web assembly 100 is cut between absorbent bodies 10 into individual taped diapers 1A having stretchable laterally opposite side portions and a non-stretchable laterally middle portion. If desired, the below-waist portion of the diaper may have its stretchability reduced or be deelasticized by application of treatment, such as heat pressing. Deelasticization of a selected portion may be effected in any kind of clothing articles according to the invention.

The same effects as in the embodiment of FIG. 4 are obtained in the embodiments illustrated in FIGS. 6 and 7, in which the stretchable first continuous web is transferred and processed after it is joined along its edge portion to the second continuous web.

While in the foregoing embodiments the joining of the edge portions of adjoining first and second continuous webs is achieved by application of an adhesive, it may be performed by heat sealing, high frequency sealing, ultrasonic sealing, or any other means. It is easier by the latter means of joining to join the edge portions of adjoining webs to each other to the very edges of the edge portions and to produce a clothing article with better appearance in a stable manner.

The clothing articles that can be produced by the method of the invention typically include absorbent articles designed to absorb and retain body fluids, such as pull-on or open-type or taped disposable diapers, pants type sanitary napkins, and incontinence pads. The clothing articles also include undergarments, such as briefs and undershirts, and other articles of clothing, like T-shirts, blouses, and dress or sport shirts. For example, the foregoing embodiments may be applied without using an absorbent body to the manufacture of disposable panty type underwear.

With respect to details that have not been described for one embodiment, the corresponding details of other embodiments appropriately apply, and the particulars described as being characteristic of one embodiment appropriately apply to other embodiments. Particulars of each of the aforementioned embodiments are appropriately interchangeable with each other.

INDUSTRIAL APPLICABILITY

The method of producing a clothing article according to the invention allows for accuracy in various processing operations in manufacturing a clothing article containing a stretch sheet. According to the method, a clothing article with good stretchability can be manufactured in a stable continuous manner while reducing the use of an expensive stretch sheet.

The invention claimed is:

1. A method of producing a clothing article comprising the steps of:
   (a) joining a first continuous web having stretchability in its longitudinal direction in a longitudinally stretched state along an edge portion thereof to a longitudinally substantially inextensible second continuous web to make a continuous composite sheet,
   (b) joining the composite sheet obtained in step (a) to a third continuous web only along the edges of the composite sheet and the third continuous web and a laterally middle part in the longitudinal direction to make a continuous-form outer cover and then joining the outer cover on its side to a member of the clothing article to make a web assembly, and
   (c) cutting the web assembly obtained in step (b) to length;
   wherein the first continuous web is selected from the group consisting of (1) a sheet having an elastic fiber layer and an extensible fiber layer united to one or both sides of the elastic fiber layer, (2) a sheet having an elastic net sheet and an extensible fiber layer united to one or both sides of the elastic net sheet, (3) a sheet having an elastic film and an extensible fiber layer united to one or both sides of the elastic film, and (4) a stretch sheet having an extensible nonwoven fabric and a large number of elastic filaments arranged to extend in one direction without intersecting with each other and bonded to the extensible nonwoven fabric over their whole length in their substantially nonstretched state.

2. The method according to claim 1, wherein step (a) is carried out using an adhesive.

3. The method according to claim 1, further comprising the step of transversely spreading the composite sheet to correct a wrinkle and transverse contraction before step (b), and wherein step (b) is carried out with the composite sheet being in the transversely spread state.

4. The method according to claim 1, wherein step (a) is carried out by joining the edge portion of the first continuous web to an edge portion of the second continuous web.

5. The method according to claim 1, further comprising a subsequent step after step (b) of securing an absorbent body is secured to the outer cover to make a continuous-form absorbent article, and further subsequent step (c) is the step of cutting the continuous-form absorbent article into individual absorbent diapers as a clothing article.

6. The method according to claim 1, further comprising the step of forming a leg opening to the composite sheet obtained by the joining step of the first and second continuous webs.

7. The method according to claim 1, wherein step (a) is carried out by joining both edge portions of the first continuous web to an edge portion of the second continuous web.

8. The method according to claim 1, further comprising the step of processing the first continuous web by introducing the first continuous web into a pair of intermeshing corrugated rolls having a number of ridges extending in the axial direction spacedly arranged on its periphery.

9. The method according to claim 1, further comprising the step of processing a non-stretch web or low-stretch web to obtain the first continuous web.

10. The method according to claim 1, wherein the first continuous web is the sheet (1) wherein the extensible fiber layer is united to both sides of the elastic fiber layer.

* * * * *